United States Patent
Tan et al.

(10) Patent No.: US 11,097,004 B2
(45) Date of Patent: Aug. 24, 2021

(54) COMPOSITION FOR IMMUNOTHERAPY AND PREPARATION METHOD THEREOF

(71) Applicant: Baden R&D Laboratories GmbH, Edenkoben (DE)

(72) Inventors: Kor Seng @ Chan Kok Seng Tan, Edenkoben (DE); Bi Fah Wong, Edenkoben (DE)

(73) Assignee: BADEN R&D LABORATORIES GMBH, Edenkoben (DE)

( * ) Notice: Subject to any disclaimer, the term of this patent is extended or adjusted under 35 U.S.C. 154(b) by 127 days.

(21) Appl. No.: 16/621,517

(22) PCT Filed: Aug. 20, 2019

(86) PCT No.: PCT/MY2019/050045
§ 371 (c)(1),
(2) Date: Dec. 11, 2019

(87) PCT Pub. No.: WO2021/025551
PCT Pub. Date: Feb. 11, 2021

(65) Prior Publication Data
US 2021/0038712 A1    Feb. 11, 2021

(51) Int. Cl.
*A61K 39/39* (2006.01)
*A61K 39/00* (2006.01)

(52) U.S. Cl.
CPC .... *A61K 39/39* (2013.01); *A61K 2039/55505* (2013.01); *A61K 2039/55516* (2013.01)

(58) Field of Classification Search
None
See application file for complete search history.

(56) References Cited

U.S. PATENT DOCUMENTS

| 2004/0001847 A1 | 1/2004 | Lasalvia-Prisco |
| 2004/0234513 A1 | 11/2004 | See |

FOREIGN PATENT DOCUMENTS

WO    WO2018138682 A1    8/2018

OTHER PUBLICATIONS

Lasalvia-Prisco, E., et al., "Mechanism of action for antitumoral activity of autologous heterotopic transplant of peripheral blood in non-small cell lung cancer", European Journal of Cancer, Sep. 2011, vol. 47, Supplement 1, p. S616, Abstract No. 9079.
Sims; "Sipuleucel-T: Autologous Cellular Immunotherapy for Men with Asympto-matic or Minimally Symptomatic Metastatic Castrate Resistant Prostate Cancer"; Journal of Cancer; 2011; 2: 357-359.
Charron; "Autologous white blood cell transfusion: Toward a younger immunity"; Human Immunology (2007) 68, 805-812.
Van Gool, S., et al., "Can multimodal immunotherapy replace radiochemotherapy in completely resected adult GBM?", Neuro-Oncology, Jun. 2017, vol. 19, Supplement 4, p. iv23, Abstract No. HGG-05 Whole document.
Gerald Dieter Griffin et al., "Autologous white blood cell infusion for trauma, brain trauma, stroke and select immune dysfunction co-morbidities: A promising and timely proposal?", Medical Hypotheses 117 (2018) 7-15, Journal homepage: www.elsevier.com/locate/mehy, pp. 7-15, May 2018.
Bucktrout, S., et al., "Recent advances in immunotherapies: from infection and autoimmunity, to cancer, and back again", Genome Medicine, Oct. 2018, vol. 10, Article No. 79, pp. 1-10 Whole document, particularly pp. 7-8.

*Primary Examiner* — Michelle S Horning
(74) *Attorney, Agent, or Firm* — Muncy, Geissler, Olds and Lowe, P.C.

(57) ABSTRACT

The present invention provides a serum and its blood components isolated from blood, wherein the blood is drawn from body of a patient, and a normal saline solution mixed with the serum and its blood components, characterized in that a Reagent A having at least one type of adjuvant, and a Reagent B having at least one type of transfer factor peptide and a buffered saline, and Reagent C having an alpha lipoic acid are added to the mixture of the serum and its blood components and the normal saline solution, such that the composition enhances cell-mediated immunity and T suppressor cells in the patient to act against autoimmune disease. The present invention also provides a method for producing such composition for immunotherapy thereof.

23 Claims, No Drawings

COMPOSITION FOR IMMUNOTHERAPY AND PREPARATION METHOD THEREOF

CROSS-REFERENCE TO RELATED APPLICATIONS

This application is the U.S. national phase of PCT Application PCT/MY2019/050045 filed on Aug. 20, 2019, which claims a priority to Malaysian Patent Application No. PI2019004519 filed on Aug. 6, 2019, the disclosures of which are incorporated in their entirety by reference herein.

FIELD OF INVENTION

The present invention generally relates to a biomedical product for immunotherapeutic treatments and the preparation of its composition.

BACKGROUND OF THE INVENTION

In general, there are two types of adaptive immunity, known as: i) humoral immunity and ii) cell-mediated immunity. Humoral immunity is mediated by B cells involving the secretion of antibodies with the aid of helper T cells. Cell mediated immunity is mediated by T cells, such as helper T cells and cytotoxic T cells. Regulatory (or suppressor) T cells, a subset of helper T ($T_h$) cells; play an important role in the suppression of the continued activity of the immune system and autoreactive T cells.

The immune system is a complex network and dysregulation of the immune system will arise with allergic disorders and autoimmune diseases. There has been a parallel increase in allergic and autoimmune disorders in recent decades suggesting that these diseases may share the same mechanisms and aetiologies. This observation is in apparent contrast to the understanding of allergy and autoimmune diseases as representatives of distinct immunological diseases as representatives of distinct immunological disorders with counteracting underlying immune mechanisms. Autoimmune diseases are in general thought to act through a $T_h1/T_h17$-driven cell mediated response, while allergies encompass a $T_h2$-mediated response.

When the immune system fails to distinguish between self and nonself, followed by the overactive immune response and the failure or suppressive function of suppressor T cells; lead to the manifestation of autoimmune diseases. On the other hand, allergy is caused by over responsiveness of the immune system resulting in hypersensitivity reactions (divided into type I, II, III and IV) in response to allergens. Both allergic disorders and autoimmune disease can occur simultaneously in the same patient. Several types of autoimmune diseases such as rheumatoid arthritis, systemic lupus erythematous have hypersensitivities as part of their pathogenesis as they were reported to cross react with immunoglobulin E (IgE) antibodies.

Conventional methods for the treatment of medical conditions, such as eczema, include topical application of moisturizers in conjunction with the application of coal tar and/or topical application of corticosteroids. Types of corticosteroids available in the market include desonide, hydrocortisone, clobetasol proprionate, mometasone furoate, bethamethasone diproprionate and many more. In addition, oral antihistamines, antibiotics even steroids (for example, prednisolone) are sometimes prescribed by the medical practitioner depending on the patient's condition. When the medical condition does not improve with the application of lotions and topical corticosteroids, immunotherapy, such as allergy shots or sublingual immunotherapy may be prescribed. As for the case of autoimmune diseases, they are traditionally managed by the administration of immunosuppressing drugs. However, the use of these immunosuppressing drugs often comes with undesirable side effects associated with toxicities or development of other conditions.

Nowadays, recent advances in immunotherapy have become of great interest to physicians, particularly in view of its lower toxicities and increased specificity. Much research has been ongoing to develop immunotherapeutic products that are more effective and efficient in combating allergic or autoimmune medical conditions, such as sinusitis, allergic rhinitis, asthma, eczema, psoriasis, rheumatoid arthritis, systemic lupus erythematosus.

Autologous active specific immunotherapy (AASI) is an autologous immunomodulating therapy which induce the production of anti-idiotypic antibodies and the modulation of regulatory T cells, followed by neutralizing and inhibit the secretion of autoantibodies, resulting in a balance immune modulating network. The present invention relates to the development of a method to produce composition(s) for the application of the use of active specific immunotherapy, which is more specific and effective against a targeted ailment especially for the treatment of autoimmune diseases and allergic disorders.

SUMMARY OF THE PRESENT INVENTION

The present invention features a composition for immunotherapy, comprising an isolated serum and its blood components of blood drawn from a patient and a normal saline solution mixed with serum and its blood components. Then, a Reagent A having at least one type of adjuvant, and a Reagent B having at least one type of transfer factor peptide and a buffered saline, and Reagent C having an alpha lipoic acid are added to the mixture of the serum and its contents and the normal saline solution, such that the composition enhances cell-mediated immunity and T suppressor cells in the patient to act against autoimmune diseases and allergic disorders.

Preferably, the serum and its blood components with the saline solution is homogenized at 40-50 rotations per minute for 15-25 seconds.

Preferably, the homogenized serum and its blood components with the saline solution is depolarized using electrical voltage at 3.2 volts. Further, the homogenized and depolarized serum and its blood components with the saline solution is preferably sterilized using ozone gas.

Preferably, the adjuvant is aluminium adjuvant or silicic adjuvant. Further, the transfer factor peptide is immune modulating transfer factor peptide.

Preferably, the buffered saline is phosphate buffered saline.

Preferably, the ratio of transfer factor peptide to buffered saline in reagent B is 1:9 or 2:8.

Further, the alpha lipoic acid is an immune modulating alpha lipoic acid. Preferably, the concentration of the alpha lipoic acid in the Reagent C is 20-25 mg/ml.

The present invention also relates to a method for producing a composition for immunotherapy, comprising steps of drawing blood from patient, allowing a serum and its blood components to develop from the drawn blood and mixing the serum and its blood components with normal saline solution, adding a Reagent A having at least one type of adjuvant to the mixture of serum and its blood components and normal saline solution, and adding a Reagent B having at least one type of transfer factor peptide and a buffered saline to the mixture of serum and its blood components, normal saline solution and Reagent A and adding a Reagent C having an alpha lipoic acid.

Preferably, the serum and its blood components to develop from the drawn blood at room temperature.

Preferably, the serum and its blood components and the normal saline solution is homogenized at 40-50 rotations per minute for 15-25 seconds.

Preferably, the homogenized serum and its blood components with the saline solution is depolarized using electrical voltage at 3.2-4.2 volts to enhance its electronic donating capacity. Further, the homogenized and depolarized serum and its blood components with the saline solution is preferably sterilized using ozone gas.

Preferably, the adjuvant is aluminium adjuvant or silicic adjuvant. Further, the transfer factor peptide is immune modulating transfer factor peptide.

Preferably, the buffered saline is phosphate buffered saline.

Preferably, the ratio of transfer factor peptide to buffered saline in reagent B is 1:9 or 2:8.

Further, the alpha lipoic acid is an immune modulating alpha lipoic acid. Preferably, wherein concentration of the alpha lipoic acid in the Reagent C is 20-25 mg/ml.

The present invention consists of features and a combination of features hereinafter fully described, it being understood that various changes in the details may be made without departing from the scope of the invention or sacrificing any of the advantages of the present invention.

DETAILED DESCRIPTION OF THE INVENTION

The general principles of the present invention relate to a method to produce composition(s) for the application of autologous active specific immunotherapy (AASI) to treat diseases. The AASI therapy is an autologous immunomodulating therapy that attempts to regulate the immune system by re-educating host defence mechanisms and provide protection to the body. It is also applicable for the treatment of cancer cases of the liver, stomach, pancreas, breast, prostate, intestine, lymphatic glands and melanoblastomas. It can also be used for the treatment of a variety of allergic disorders, for example, eczema and autoimmune diseases such as rheumatoid arthritis by immunomodulating the human body system.

Additional biological compound like MF+"Mito Organelles" Super Transfer Factor (MF+MO STF) were prescribed for the treatment of eczema. MF+MO STF are small immune messenger molecules, passing immunity information and how to properly respond, from one immune cell to another immune cell. They are universal immunocorrectors as they induce (when applicable as in cancer), suppress and normalize immune response. Once released, they will stimulate the activity of cell-mediated immunity and natural killer (NK) cells to act against bacterial, viral and parasitic infections.

Addition of biological compound like alpha lipoic acid (or α-lipoic acid, ALA), a potent antioxidant that has been reported to have immune-modulating properties in autoimmune disease either directly or indirectly, such as through the regulation of T cell and B cell proliferation and function. These properties of alpha lipoic acid may be beneficial to counter both oxidative stress and immune dysfunction, which are believed to participate in the development and progression of autoimmune disease such as systemic lupus erythematosus (SLE), rheumatoid arthritis (RA), and primary vasculitis, as well as multiple sclerosis (MS).

The composition for the AASI is produced by first obtaining serum and its blood components from a patient's blood, followed by homogenization, depolarization, sterilization, and eventually mixture with Reagents A, B and C, as follows:

Serum and its Blood Components

Blood, mandatory autologous blood, is drawn from a patient suffering from a targeted disease using a sterile needle and syringe. The syringe containing the drawn blood is stored at room temperature and at an upright position with the plunger facing upwards. A serum and its blood components should be visible within 3 days. Then, the blood sample is transferred to another sterile vessel, such as a Petri dish, in which the serum and its blood components are isolated.

Homogenization, Depolarization and Sterilization

The isolated serum and its blood components are added with a normal saline solution (0.9% w/v sodium chloride), preferably at a serum and its blood components to normal saline ratio of 1:10, and then homogenized using a tissue homogenizer at 40-50 revolutions per minute (rpm), preferably 40 rpm, for 15-25 seconds, preferably 20 seconds.

After that, the homogenized mixture is depolarized using an electrical voltage, for example, using a multimeter, at 3.2-4.2 volts to give an electrical balance and neutrality between the cellular membranes by reducing negative charge in cells.

Optionally, the depolarized mixture is then injected with 60-80 μg/mL, preferably 60 μg/m L, ozone gas for sterilization purpose.

Reagent A

Reagent A is a reagent containing at least one type of adjuvant or serum activator, such as aluminium or silicic adjuvants, which converts the autoantibodies present in patients with autoimmune disease to specific immunogens. Other adjuvants may be alum, aluminium hydroxide, aluminium phosphate, calcium phosphate hydroxide, squalene, plant saponins, cytokines, food-based oil, or a combination thereof. The immunogens are recognized by the patient's own immune system and it forms anti-idiotypic antibodies against the immunogens in reaction and autoantibodies to maintain homeostasis. Reagent A is added and mixed well into the depolarized mixture.

Reagent B

Reagent B contains 10-20% v/v, preferably 10% v/v, transfer factor peptides, preferably immune activating transfer factor peptides (or dialysable leukocyte extract), and 80-90% v/v, preferably 90% v/v, buffered saline, preferably phosphate buffered saline. This means that the ratio of transfer factor peptides to buffered saline is 1:9 or 2:8. In an embodiment of the present invention, the immune activating transfer peptides leporine-derived, low molecular weight (~10 kDa and 3 nm) transfer factors. The functions of immune activating transfer factor peptides are to increase immunity and increase reactivity towards antigenic stimuli. They contain suppressor factor in preventing immune overreactions and are useful in managing autoimmune disease. Once released, they will modulate the activity of cell-mediated immunity and T suppressor cells to act against allergic disorders. The phosphate buffered saline contains sodium chloride, sodium phosphate, and (in some formulations) potassium chloride and potassium phosphate. Alternatively, borate buffered saline, bicarbonate buffered saline and sodium buffered saline may be used instead of the phosphate buffered saline. Reagent B is added and mixed well into the depolarized mixture containing Reagent A.

Reagent C

Reagent C contains 20-25 mg/ml of alpha lipoic acid, which is a potent antioxidant, by the regulation of T cell and B cell proliferation and function. Reagent C is added and mixed well into the depolarized mixture containing Reagent A and Reagent B to produce the final composition for immunotherapy of the targeted disease.

Aliquot of Final Composition

Prior to use, the final composition of 1.1 mL is aliquoted into vials of 2.5 mL size, which are then stored at 4-16° C. when not in use.

More specifically, the contents of individual components making up the final composition for immunotherapy is described in the following examples of embodiment (before the step of aliquoting into vials):

Example 1

The composition for immunotherapy comprises:
2.5-3.5 mL of isolated serum and its blood components from 30-35 mL (preferably 30 mL) of blood
25-35 mL of normal saline solution, preferably 30 mL
60-80 µg/mL ozone gas, preferably 60 µg/mL
3 mL of Reagent A
3 mL of Reagent B
3 mL of Reagent C Example 2

The composition for immunotherapy comprises:
2.5 mL of isolated serum and its blood components from 30 mL of blood
25 mL of normal saline solution
60 µg/mL ozone gas
3 mL of Reagent A
3 mL of Reagent B
3 mL of Reagent C Example 3

The composition for immunotherapy comprises:
3.0 mL of isolated serum and its blood components from 30 mL of blood
30 mL of normal saline solution
60 µg/mL ozone gas
3 mL of Reagent A
3 mL of Reagent B
3 mL of Reagent C Example 4

The composition for immunotherapy comprises:
3.5 mL of isolated serum and its blood components from 30-35 mL of blood
35 mL of normal saline solution
60 µg/mL ozone gas
3 mL of Reagent A
3 mL of Reagent B
3 mL of Reagent C Example 5

The composition for immunotherapy comprises:
2.5 mL of isolated serum and its blood components from 30 mL of blood
25 mL of normal saline solution
61-70 µg/mL ozone gas
3 mL of Reagent A
3 mL of Reagent B
3 mL of Reagent C Example 6

The composition for immunotherapy comprises:
3.0 mL of isolated serum and its blood components from 30 mL of blood
30 mL of normal saline solution
61-70 µg/mL ozone gas
3 mL of Reagent A
3 mL of Reagent B
3 mL of Reagent C Example 7

The composition for immunotherapy comprises:
3.5 mL of isolated serum and its blood components from 30-35 mL of blood
35 mL of normal saline solution
61-70 µg/mL ozone gas
3 mL of Reagent A
3 mL of Reagent B
3 mL of Reagent C Example 8

The composition for immunotherapy comprises:
2.5 mL of isolated serum and its blood components from 30 mL of blood
25 mL of normal saline solution
71-80 µg/mL ozone gas
3 mL of Reagent A
3 mL of Reagent B
3 mL of Reagent C Example 9

The composition for immunotherapy comprises:
3.0 mL of isolated serum and its blood components from 30 mL of blood
30 mL of normal saline solution
71-80 µg/mL ozone gas
3 mL of Reagent A
3 mL of Reagent B
3 mL of Reagent C Example 10

The composition for immunotherapy comprises:
3.5 mL of isolated serum and its blood components from 30-35 mL of blood
35 mL of normal saline solution
71-80 µg/mL ozone gas
3 mL of Reagent A
3 mL of Reagent B
3 mL of Reagent C The present invention may be embodied in other specific forms without departing from its essential characteristics. The described embodiments are to be considered in all respects only as illustrative and not restrictive. The scope of the invention is, therefore indicated by the appended claims rather than by the foregoing description. All changes, which come within the meaning and range of equivalency of the claims, are to be embraced within their scope.

The invention claimed is:

1. A composition for immunotherapy, comprising:
   a serum and its blood components isolated from blood, wherein the blood is drawn from body of a patient; and
   a normal saline solution mixed with the serum and its blood components,
   characterized in that a Reagent A having at least one type of adjuvant, and a Reagent B having at least one type of transfer factor peptide and a buffered saline, and Reagent C having an alpha lipoic acid are added to the mixture of the serum and its blood components and the normal saline solution, such that the composition enhances cell-mediated immunity and T suppressor cells in the patient to act against autoimmune disease.

2. A composition for immunotherapy of claim 1, wherein the serum and its blood components and the normal saline solution is homogenized at 40-50 rotations per minute for 15-25 seconds.

3. A composition for immunotherapy of claim 2, wherein the homogenized serum and its blood components with the saline solution is depolarized using electrical voltage at 3.2-4.2 volts.

4. A composition for immunotherapy of claim 3, wherein the homogenized and depolarized serum and its blood components with the saline solution is sterilized using ozone gas.

5. A composition for immunotherapy of claim 1, wherein the serum and its blood components with the normal saline solution is mixed at a serum and its blood components to normal saline ratio of 1:10.

6. A composition for immunotherapy of claim 1, wherein the adjuvant is aluminium adjuvant or silicic adjuvant.

7. A composition for immunotherapy of claim 1, wherein the transfer factor peptide is immune activating transfer factor peptide.

8. A composition for immunotherapy of claim 1, wherein the buffered saline is phosphate buffered saline.

9. A composition for immunotherapy of claim 1, wherein the ratio of transfer factor peptide to buffered saline in reagent B is 1:9 or 2:8.

10. A composition for immunotherapy of claim 1, wherein the alpha lipoic acid is an immune modulating alpha lipoic acid.

11. A composition for immunotherapy of claim 1, wherein concentration of the alpha lipoic acid in the Reagent C is 20-25 mg/ml.

12. A method for producing a composition for immunotherapy, comprising steps of:
    drawing blood from patient;
    isolating a serum and its blood components developed from the drawn blood;
    mixing the serum and its blood components with a normal saline solution;
    adding a Reagent A having at least one type of adjuvant to the mixture of serum and its blood components with normal saline solution; and
    adding a Reagent B having at least one type of transfer factor peptide and a buffered saline to the mixture of serum and its blood components, normal saline solution and reagent A; and
    adding a Reagent C having an alpha lipoic acid to the mixture of serum and its blood components and normal saline solution.

13. A method for producing a composition for immunotherapy of claim 12, wherein the serum and its blood components develops from the drawn blood at room temperature.

14. A method for producing a composition for immunotherapy of claim 12, wherein the serum and its blood components with the normal saline solution is homogenized at 40-50 rotations per minute for 15-25 seconds.

15. A method for producing a composition for immunotherapy of claim 14, wherein the homogenized serum and its blood components with the saline solution is depolarized using electrical voltage at 3.2-4.2 volts.

16. A method for producing a composition for immunotherapy of claim 15, wherein the homogenized and depolarized serum and its blood components with the saline solution is sterilized using ozone gas.

17. A method for producing a composition for immunotherapy of claim 12, wherein the serum and its blood components with the normal saline solution is mixed at a serum and its blood components to normal saline ratio of 1:10.

18. A method for producing a composition for immunotherapy of claim 12, wherein the adjuvant is aluminium adjuvant or silicic adjuvant.

19. A method for producing a composition for immunotherapy of claim 12, wherein the transfer factor peptide is immune activating transfer factor peptide.

20. A method for producing a composition for immunotherapy of claim 12, wherein the buffered saline is phosphate buffered saline.

21. A method for producing a composition for immunotherapy of claim 12, wherein the ratio of transfer factor peptide to buffered saline in reagent B is 1:9 or 2:8.

22. A method for producing a composition for immunotherapy of claim 12, wherein the alpha lipoic acid is an immune modulating alpha lipoic acid.

23. A method for producing a composition for immunotherapy of claim 12, wherein concentration of the alpha lipoic acid in the Reagent C is 20-25 mg/ml.

* * * * *